US010456321B2

(12) United States Patent
Shadduck

(10) Patent No.: US 10,456,321 B2
(45) Date of Patent: Oct. 29, 2019

(54) FLUID SKIN TREATMENT SYSTEMS AND METHODS

(71) Applicant: John H. Shadduck, Menlo Park, CA (US)

(72) Inventor: John H. Shadduck, Menlo Park, CA (US)

( * ) Notice: Subject to any disclaimer, the term of this patent is extended or adjusted under 35 U.S.C. 154(b) by 0 days.

(21) Appl. No.: 15/247,835

(22) Filed: Aug. 25, 2016

(65) Prior Publication Data

US 2017/0056636 A1    Mar. 2, 2017

Related U.S. Application Data

(60) Provisional application No. 62/209,641, filed on Aug. 25, 2015.

(51) Int. Cl.
| *A61M 35/00* | (2006.01) |
| *A61H 9/00* | (2006.01) |
| *A61M 1/00* | (2006.01) |
| *A61H 23/02* | (2006.01) |
| *A61B 17/32* | (2006.01) |

(52) U.S. Cl.
CPC ........... *A61H 9/0057* (2013.01); *A61H 23/02* (2013.01); *A61M 1/0088* (2013.01); *A61B 2017/320004* (2013.01); *A61B 2017/32007* (2017.08)

(58) Field of Classification Search
CPC ................ A61H 9/0057; A61H 9/0021; A61H 2201/105; A61M 1/0084; A61M 1/088; A61B 17/54; A61B 17/320068; A61B 2217/007; A61B 2217/005; A61B 2017/320004

See application file for complete search history.

(56) References Cited

U.S. PATENT DOCUMENTS

| 2004/0092959 A1* | 5/2004 | Bernaz | A61B 17/54 606/131 |
| 2009/0157094 A1* | 6/2009 | Yeshurun | A61B 17/54 606/131 |
| 2013/0002411 A1* | 1/2013 | Henderson | H02N 2/005 340/407.1 |
| 2013/0158547 A1* | 6/2013 | David | A61B 18/14 606/41 |

* cited by examiner

*Primary Examiner* — Anh T Dang
(74) *Attorney, Agent, or Firm* — Levine Bagade Han LLP

(57) ABSTRACT

The present invention relates to devices for dermatology and more particularly to fluid enhanced skin treatment system for skin rejuvenation that can optionally use an abrasive probe for removing epidermal layers while contemporaneously providing for the infusion of therapeutic fluids into the skin.

17 Claims, 15 Drawing Sheets

FLUID SKIN TREATMENT SYSTEMS AND METHODS

CROSS-REFERENCE TO RELATED APPLICATION

This application claims benefit of priority to U.S. Provisional Application No. 62/209,641 filed Aug. 25, 2015, the contents of which is herein incorporated by reference in its entirety.

FIELD OF THE INVENTION

The present invention relates to devices for dermatology and more particularly to fluid enhanced skin treatment system for skin rejuvenation that can optionally use an abrasive probe for removing epidermal layers while contemporaneously providing for the infusion of therapeutic fluids into the skin.

BACKGROUND OF THE INVENTION

Dermatologists and plastic surgeons have used various methods for removing superficial skin layers to cause the growth of new skin layers (i.e., commonly described as skin resurfacing techniques) since the early 1900's. Early skin resurfacing treatments used an acid such as phenol to etch away surface layers of a patient's skin that contained damage to thereafter be replaced by new skin. The term damage when referring to a skin disorder is herein defined as any cutaneous defect, e.g., including but not limited to rhytides, hyperpigmentation, acne scars, solar elastosis, other dyschromias, stria distensae, seborrheic dermatitus.

Following the removal of surface skin layers at a particular depth, no matter the method of skin removal, the body's natural wound-healing response begins to regenerate the epidermis and underlying wounded skin layers. The new skin layer will then cytologically and architecturally resemble a younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis, and (iii) deep resurfacing treatments that remove tissue to the depth of the reticular dermis.

Modern techniques for skin layer removal include: $CO_2$ laser resurfacing which fails into the category of a deep resurfacing treatment; Erbium laser resurfacing which generally is considered a medium-depth treatment; mechanical dermabrasion using high-speed abrasive wheels which results in a medium-depth or deep resurfacing treatment; and chemical peels which may range from a superficial to a deep resurfacing treatment, depending on the treatment parameters. A recent treatment, generally called micro-dermabrasion, has been developed that uses an air-pressure source to deliver abrasive particles directly against a patient's skin at high-velocities to abrade away skin layers. Such a micro-dermabrasion modality may be likened to sandblasting albeit at velocities that do no cause excess pain and discomfort to the patient. Micro-dermabrasion as currently practiced falls into the category of a superficial resurfacing treatment.

A superficial exfoliation, peel or abrasion removes some or all of the epidermis may be suited for treating very light rhytides. Such a superficial exfoliation is not effective in treating many forms of damage to skin. A medium-depth resurfacing treatment that extends into the papillary dermis can treat many types of damage to skin. Deep resurfacing treatments, such as $CO_2$ laser treatments, that extend well into the reticular dermis causes the most significant growth of new skin layers but carry the risk of scarring unless carefully controlled.

It is useful to briefly explain the body's mechanism of actually resurfacing skin in response to the removal of a significant depth of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticuilar dermis, which is sustained by angiogenesis and protected anteriorly by the reforming epithelial layer. The new extracellular matrix is largely composed of collagen fibers (particularly Types I and III) which are laid down in compact parallel arrays. It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal architecture of the dermal layers. It is well recognized that there will be a clinical improvement in the condition and appearance of a patient's skin when a more normal architecture is regenerated by the body's wound-healing response. Of most significance to a clinical improvement in skin is the creation of more dense parallel collagen aggregates with decreased periodicity (spacing between fibrils). The body's wound-healing response is responsible for synthesis of these collagen aggregates. In addition to the body's natural wound healing response, adjunct pharmaceutical treatments that are administered concurrent with, or following, a skin exfoliations can enhance the development of collagen aggregates to provide a more normal dermal architecture in the skin—the result being a more youthful appearing skin.

The deeper skin resurfacing treatments, such as laser ablation, chemical peels and mechanical dermabrasion have drawbacks. The treatments are best used for treatments of a patient's face and may not be suited for treating other portions of a patient's body. For example, laser resurfacing of a patient's neck or decolletage may result in post-treatment pigmentation disorders. All the deep resurfacing treatments are expensive, require anesthetics, and must be performed in a clinical setting. Perhaps, the most significant disadvantage to deep resurfacing treatments relates to the post-treatment recovery period. It may require up to several weeks or even months to fully recover and to allow the skin the form a new epidermal layer. During a period ranging from a few weeks to several weeks after a deep resurfacing treatment, the patient typically must wear heavy make-up to cover redness thus making the treatment acceptable only to women.

Conventional dry microdermabrasion uses a hand held device to jet dry abrasive particles against the skin to remove cells from the epidermis to provide a younger and healthier looking appearance, remove wrinkles and improve skin tone. The superficial treatment offered by dry microdermabrasion has the advantages of being performed without anesthetics and requiring no extended post-treatment recovery period. However, such dry microdermabrasion systems do not treat deep wrinkles and dehydrates the patient's skin.

SUMMARY OF THE INVENTION

The fluid skin treatment systems and methods corresponding to the invention relate in general to the field of skin care, and the systems may be used by an individual to treat his or her own skin or can be used by a practitioner to treat a patients skin. The systems may be used to perform dermabrasion, skin rejuvenation, cleansing and the infusion of treatment fluids into the skin.

In one variation, the system provides new modalities of fluid enhanced dermabrasion which improve upon the devices and methods disclosed by the author in U.S. Pat. Nos. 6,644,591; 7,678,120; 7,789,886, 8,066,716 and 8,337,513, all of which are incorporated herein by this reference. A fluid enhanced microdermabrasion system includes a probe with an abrasive skin-contact surface, a negative pressure source and a treatment fluid source both in communication with the skin-contact surface. The operator translates the abrasive skin-contact surface over the patient's skin to remove an epidermal layer, and the negative pressure source suctions the skin-contact surface against the skin while at the same time drawing the treatment fluid from a source to the abraded skin surface. A combination of surface features of the skin-contact surface and the negative pressure allows the treatment fluid to penetrate surface skin layers. Such a fluid-assisted microdermabrasion treatment can remove visible lines and allow for improved absorption of topical skin treatment products.

A variation of a microdermabrasion system for treating a tissue includes a device body having an applicator end, the applicator end comprising a tissue contact surface being recessed within the applicator end; at least one fluid opening configured to deliver a fluid from the fluid source to the skin contact surface; at least one negative pressure opening configured to apply the negative pressure source therethrough to draw the tissue against the tissue contact surface, wherein, when the tissue is positioned against the applicator end, the negative pressure source pulls the fluid from the at least one fluid opening; and at least one vibratory element positioned in the device body, where actuation of the vibratory element causes a vibratory motion of the applicator end. The tissue contact surface can comprises an abrasive surface. Alternatively or in combination, the tissue contact surface comprises a plurality of annular ridges and a plurality of recesses.

In one variation, the at least one vibratory element comprises at least one vibratory element that produces vibration in a single direction relative to the device body. For example, the at least one vibratory element produces vibration the single direction that is perpendicular to an axis of the applicator end or where the at least one vibratory element produces vibration the single direction that is parallel to an axis of the applicator end.

Variations of the system can include at least a second vibratory element that produces vibration in a direction perpendicular to the single direction of the at least one vibratory element.

In another example, a microdermabrasion system can include a device body having an applicator end, the applicator end comprising a tissue contact surface comprising an abrasive finish and being recessed within the applicator end; at least one fluid opening configured to deliver a fluid from the fluid source to the tissue contact surface; at least one negative pressure opening configured to apply the negative pressure source therethrough to draw the tissue against the tissue-contact surface, wherein when the tissue is positioned against the applicator end, the negative pressure source pulls the fluid from the at least one fluid opening; and at least one vibratory element positioned in the device body, where actuation of the vibratory element configured to vibrate in a single axis, where the vibratory element causes a vibratory motion of the applicator end.

The present disclosure also includes methods for treating skin and/or tissue. For example, such a method can include advancing a device body having an applicator end against tissue, the applicator end comprises a recessed tissue contact surface; drawing suction through at least one negative pressure opening located in the recessed tissue contact surface which pulls the skin within the applicator end; and producing a first vibratory motion within the device body, where the first vibratory motion is limited to a first directional axis and where the first vibratory motion causes an abrasion on the skin resulting from the skin contacting the recessed tissue contact surface.

In one variation, drawing suction pulls a fluid through at least one fluid.

In another example, the method further comprises producing a second vibratory motion, where the second vibratory motion is limited to a second directional axis that is different than the first directional axis. The second directional axis can be perpendicular to the first directional axis. The first directional axis is parallel to a central axis of the applicator end (where the central axis extends perpendicularly to the surface of the tissue).

There remains a need for a skin treatment system that can effectively rejuvenate a patient's skin, that can optionally use abrasives for removing epidermal layers and that provides an effective means for the infusion of therapeutic fluids into the skin. Further, there is a need for a system that allows for use by aestheticians in an office setting and for use at home by the patient.

DETAILED DESCRIPTION OF THE INVENTION

Figure 1:
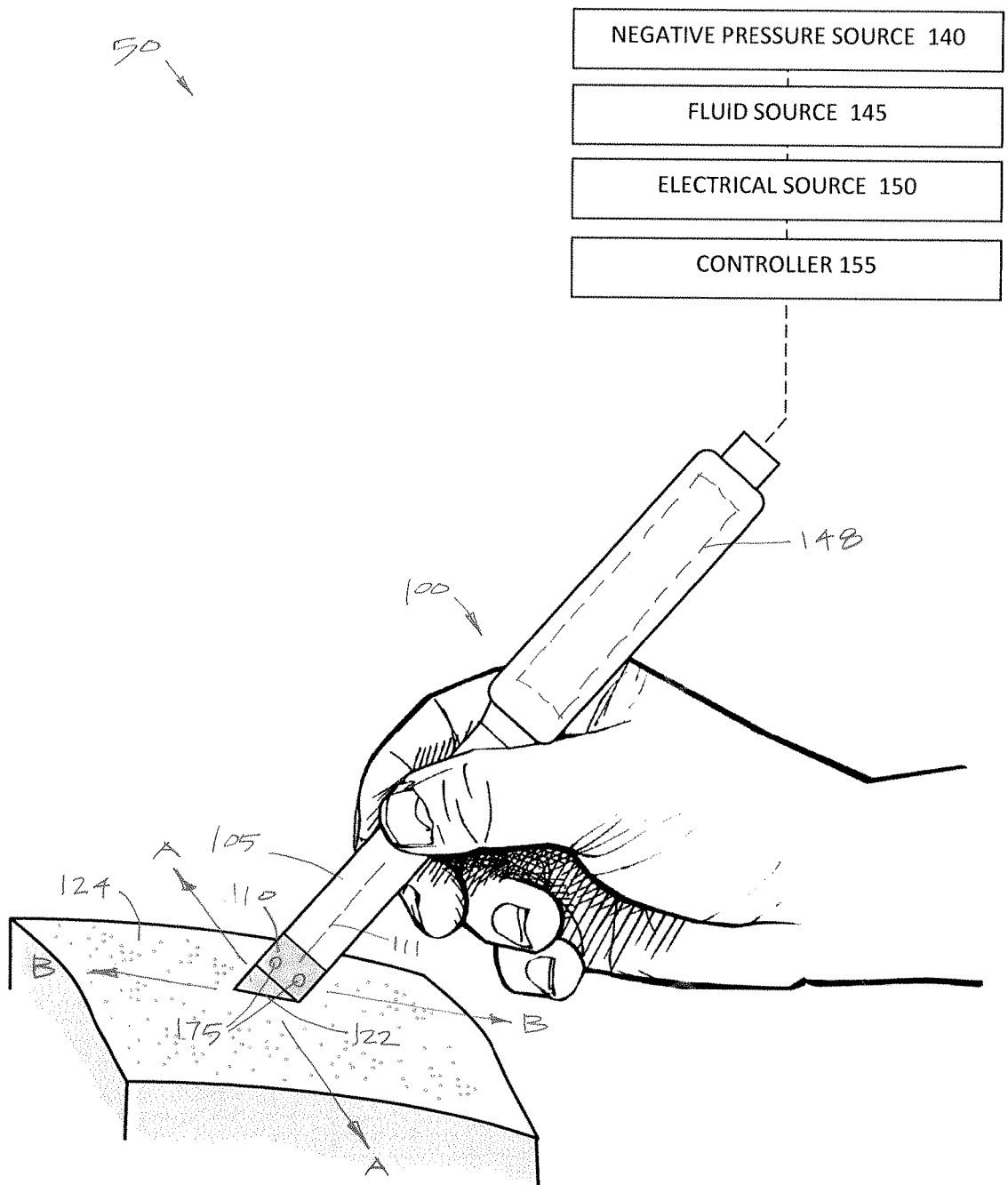
FIG. 1 is a perspective view of an embodiment of the treatment device in use being held by a human hand in relation to a patient's skin.
Figure 2:
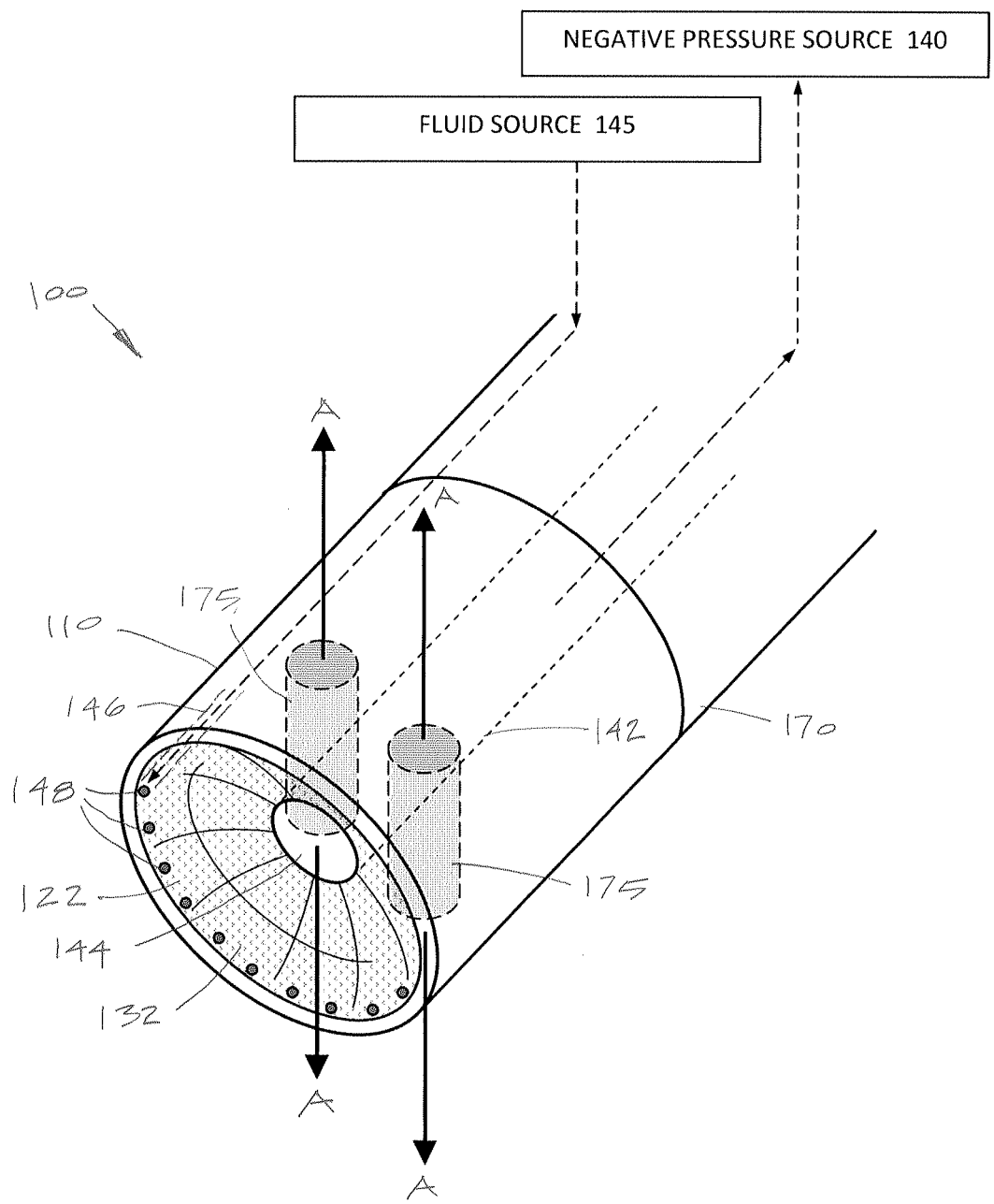
FIG. 2 is a perspective view of a working end of a device similar to that of FIG. 1 showing the location and orientation of linear actuators, fluid inflow ports and a central suction passageway in the working end.

FIGS. 1 and 2 illustrate an embodiment of the invention wherein the fluid skin treatment system 50 includes a treatment device 100 comprising a hand held unit with an elongated shaft or body 105 that can be gripped by the operator's hand and a working end or applicator tip portion 110 with a skin contact surface 122 configured to engage a patient's skin 124 (FIG. 1). The body 105 can have any suitable dimension along axis 111 and any shape suited for gripping with a human hand or fingers, and the surface area of the skin contact surface 122 can range from about 20 mm$^2$ to 100 cm$^2$. Devices with smaller dimension skin contact surfaces 122 are suited for treating facial skin, and the larger skin contact surfaces 122 are adapted for treating a patient's torso, arms or legs. In one variation described below, a practitioner may use a large surface area device (see, e.g., FIG. 6B) to treat a skin of a patient's arms, legs, torso or back in a form of fluid infusion into the epidermis, skin cleansing or a chemo-detoxification therapy.

Figure 3:
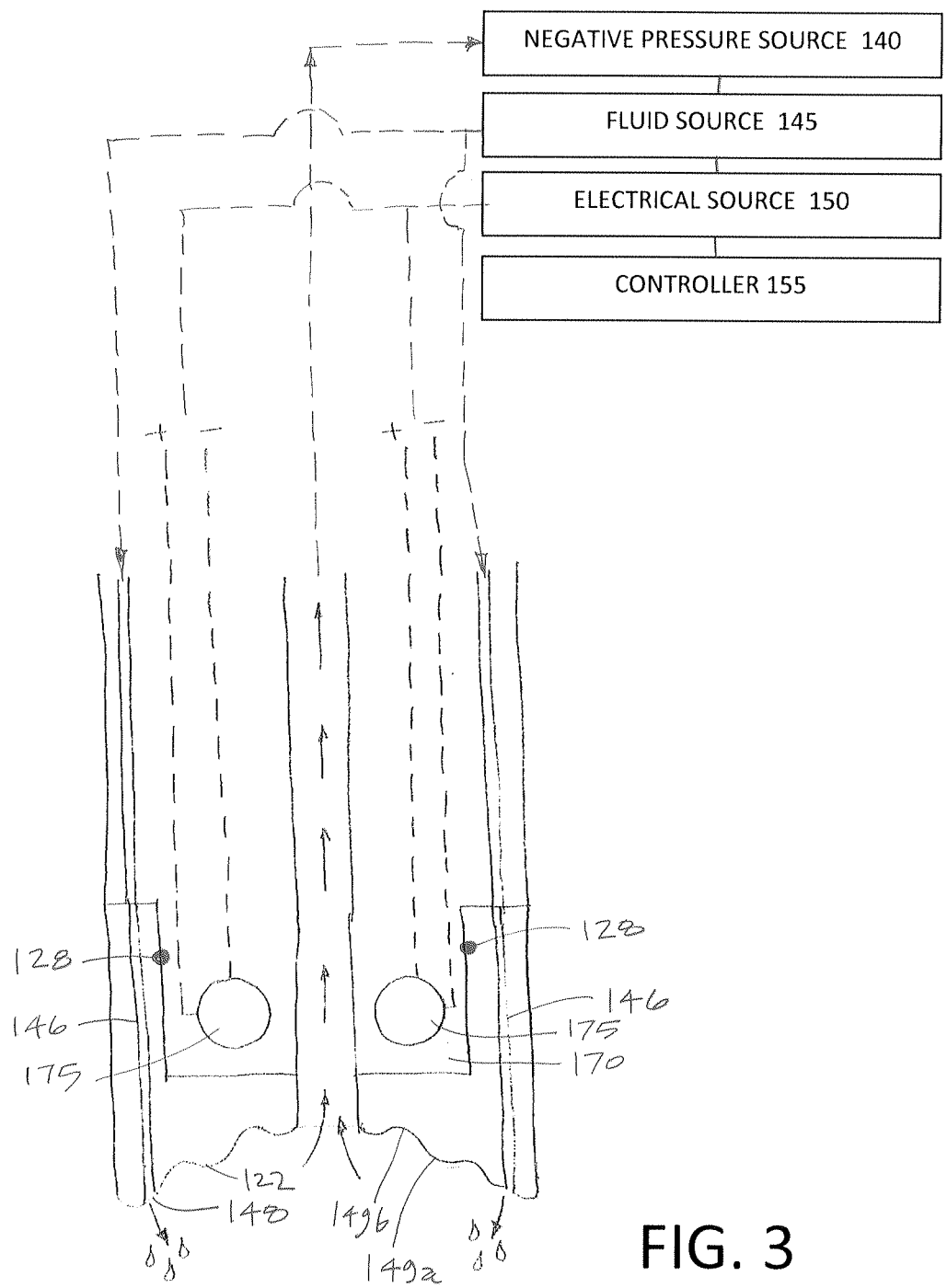
FIG. 3 is a sectional view of a working end similar to that of FIG. 2 showing the orientation of linear actuators, fluid inflow ports and a central suction passageway.

The components of device 100 as can be understood from FIGS. 1-3 include a variation of the device body 105 being fabricated of a molded plastic, metal, a combination of plastic and metal or other suitable materials. The body 105 can be disposable or re-useable, or can be a combination of disposable and non-disposable components. In the illustrated variations, the working end or applicator tip portion 110 is detachable from the device body 105 and can be coupled to the body 105 by a slip fit or friction fit with or without an O-ring 128 as can be understood from FIG. 3. Any means of detachably coupling the applicator tip 110 to the body 105 may be suitable, such as screw thread or quick-connect type fittings. In one variation, the applicator tip 110 is a substantially rigid plastic material and can be disposable. In another variation, the tip 110 is configured with at least the skin contact surface 122 comprising a soft silicone or other rubber-like material that can flex and/or compress slightly when engaging a patient's skin as will be described below.

Now referring to FIGS. 1-3, it can be seen that a variation of the system 50 includes a negative pressure source 140 that communicates with an aspiration channel 142 in the device 100 that terminates distally in an opening 144 in the skin contact surface 122. In the variation of FIG. 2, the aspiration channel 142 terminates in opening 144 in the center of skin contact surface 122, but it should be appreciated that the opening 141 can be singular or multiple and can be located or distributed anywhere in the skin contact surface 122.

The system 50 can further optionally includes a fluid source 145 that communicates with at least one flow channel 146 in the device body 110 which extend through the applicator tip 110 and terminate in a plurality of ports 148 in the skin contact surface 122 (FIG. 2). As can be seen in FIG. 2, the ports 148 are distributed around an outer perimeter of the skin contact surface 122. In this variation, the skin contact surface 122 is concave which is adapted for suctioning tissue into the concavity of the applicator tip 110. In one variation, the skin contact surface 122 can carry abrasive elements, such as diamond particles 132 embedded into the surface 122. One or more such tips 110 with abrasives can be used during a treatment of a patient's skin, with different size diamond particles in different tips for more aggressive and less aggressive dermabrasion. In a method of making an applicator tip 110, such a tip can be injection molded of a rigid plastic. Thereafter, the skin contact surface 122 can be heated to be slightly melted and then impressed within a form against diamond particles 132 which then can be somewhat embedded in the skin contact surface 122 as the plastic cools and resets. In another variation method of making an applicator tip 110, the skin contact surface 122 can be an elastomer (e.g., silicone) which can be molded into a form that carries the diamond particles will then be bonded to the surface 122. In another method, the diamond particles can be mixed with a polymer or elastomer and following a molding process, a thin layer of the polymer or elastomer can be removed (by chemical etching, sand blasting, etc) to expose the diamond particles. In another method, the diamond particles can bonded to a molded applicator tip 110 with adhesives or bonding agents.

FIG. 1 shows the fluid source 145 being remote from the handheld device 100, but it should be appreciated that the device body 105 can be dimensioned to carry a cartridge fluid source indicated at 148 in FIG. 1.

In FIG. 1, it can be seen about the plane of the skin contact surface 122 is angled about 30 to 45° from the longitudinal axis 111 of the body 105. It should be appreciated that the plane of the skin contact surface 122 can vary from about 45° to 90° from said axis 111. For convenience, FIGS. 2-3 show the skin contact surface 122 as being perpendicular to the axis 111.

In the variation in FIG. 3, it can be seen that the skin contact surface 122 in configured with a plurality of annular ridges 149a and recesses 149b which are adapted for engaging and tensioning the patient's skin under when the device is used to abrade skin, as disclosed in the author's previous patents, for example, U.S. Pat. No. 6,641,591. The ridges may be provided with sharp edges or abrasive diamond particles 132 or other abrasive elements for abrading skin.

Referring to FIGS. 1-3, the system 50 further includes an electrical source 150 and controller 155 for actuating a mechanism to impart vibratory forces from the skin contact surface 122 to the patient's skin. In FIGS. 2-3, a device 100 corresponding to the invention includes the distal portion 170 of body 105 carrying at least one linear actuator or linear resonant actuator 175 which is adapted to provide mechanical vibratory force in a particular 'single' direction (or vector). In FIG. 2, the body 105 carries two actuators 175 which are configured to produce vibratory motion as shown by arrows AA that is perpendicular to the plane of the skin contact surface 122. The variations of FIGS. 2 and 3 show first and second linear resonant actuators (LRAs) 175 carried within non-disposable body 105 closely adjacent to the disposable applicator tip 110 so that vibratory forces are transmitted directly to the applicator tip 110 and skin contact surface without any significant energy losses. To enhance coupling of vibratory forces between the device body 105 and the applicator tip 110, that can be engagement features such as keys, pins, or cooperating male-female elements and the like to effectively couple motion from the LRAs 175 to the skin contact surface 122 and then to the patients skin.

As background, the forces produced by vibration motors are actually vectors, with both a direction and a magnitude. In the configurations of skin treatment devices disclosed herein corresponding to the invention, the direction of vibratory motion provide by LRAs is designed to achieve certain objectives, which can be (i) to enhance abrasion with an abrasive applicator tip 110, or (ii) to enhance fluid infusion into the patient's skin, for example, following dermabrasion.

Figure 4A:
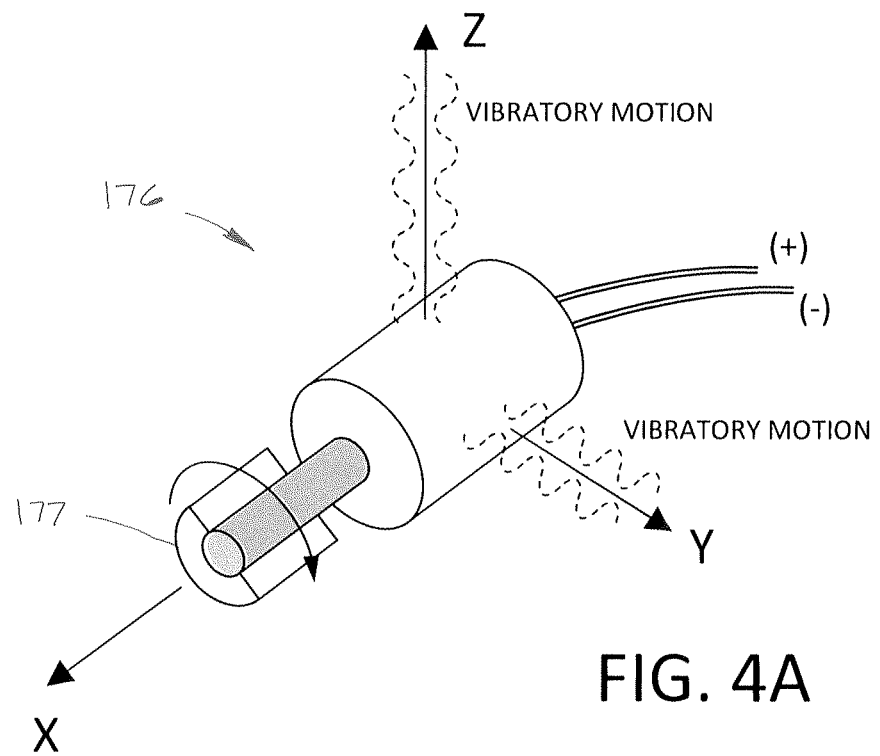
FIG. 4A is an illustration of a vibration device comprising an eccentric rotating mass (ERM) motor.

A typical type of vibration motor is an eccentric rotating mass (ERM) motor 176 as shown in FIG. 4A. This type of vibration motor operates on a direct current and carries an offset mass or non-symmetric mass 177 attached to the motor shaft. In operation, the motor rotates the eccentric weight and the centrifugal or centripetal forces are unbalanced which causes a rapid displacement of the motor resulting in as vibration. This ERM type of motor essentially then vibrates in two directions X and Y with no direct movement in the direction of the axis Z of the motor shaft. A 'coin' vibration motor works on the same principle as an article ERM motor except it is flatter and compact. The author believes that such ERM vibration motors would not be particularly effective in the present application, and therefore the use of an ERM motor is not proposed herein for several variations of skin treatment devices.

Figure 4B:
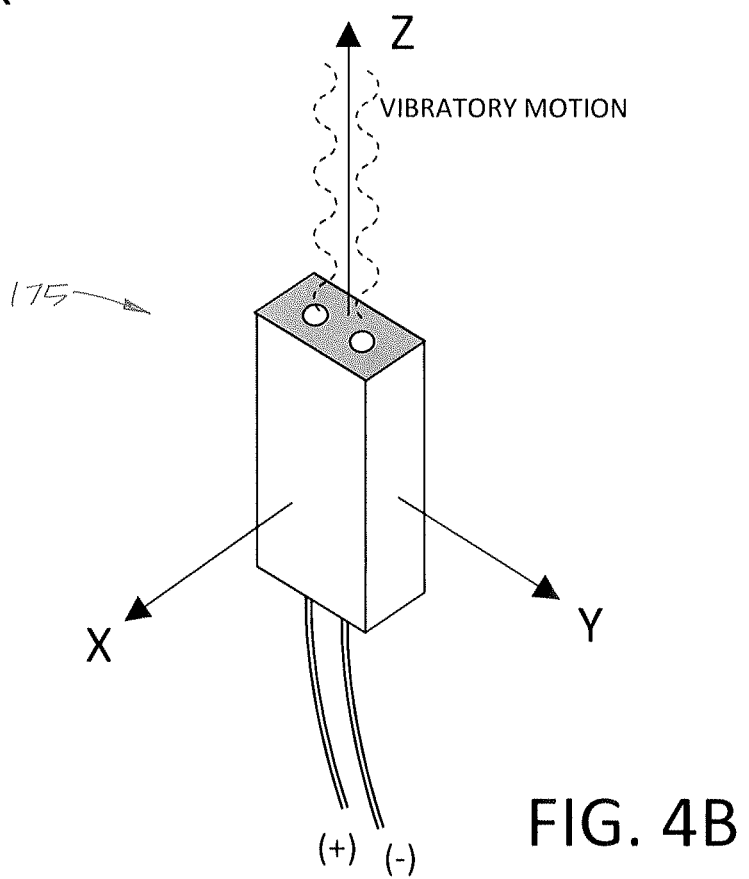
FIG. 4B is an illustration of a vibration device comprising a linear resonant actuator (LRA).

With the above background in mind, the invention herein can use one or more linear resonant actuators or LRA 175 as shown in FIG. 4B that allows for control of the vectors (direction and magnitude) of vibratory forces applied to a patient's skin. Of particular interest, the LRAs produce vibrations much differently than ERM or eccentric rotating mass motors. An LRA comprises a magnet, a spring and a voice coil that are adapted for motor displacement. The magnet is actuated by an electromagnetic field in the voice coil, and the spring enables the magnet (that has a selected mass) to oscillate back and forth around a normal rest position maintained by the spring. Thus, it can easily understood that the magnet can be restricted to move back and forth along only one axis Z in FIG. 4B. Such an LRA is adapted to be driven by an AC drive signal. Thus, in one variation described above and shown in FIGS. 2 and 3, the LRA is mounted to generate vibratory motion substantially parallel to the patient's skin (and the skin contact surface 122) in an "abrasion mode" to move the abrasive applicator tip 110 across the surface of the skin. This form of motion parallel to the skin is advantageous compared the type of motion provided by a typical ERM motor that is not capable of generating vibratory forces in a single plane.

As can be understood from FIG. 1, the device 100 and it applicator tip 110 are also adapted to be manually moved or translated across the patient's skin at the same time the LRAs provide vibratory motion. In one variation, the device includes directions for use wherein the practitioner is instructed to move the applicator tip 110 in directions perpendicular to the direction of vibratory motion provided LRAs 175. Thus, the combination of manual translation and vibratory motion allows for very effective removal of epidermal layers. As an example in FIG. 1, the directions of vibratory motion are indicated by arrows AA, and the direction of manual translation indicated by arrows BB.

Figure 5A:
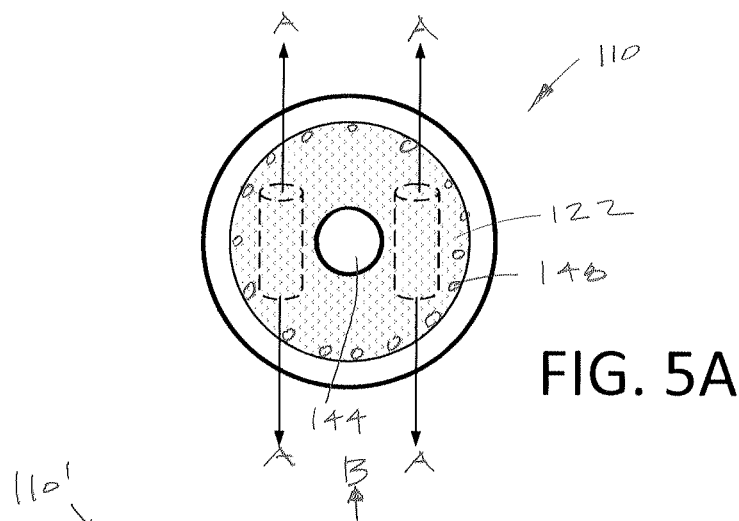
FIG. 5A is a front elevation view of the working end of FIG. 2 again showing the location and orientation of linear actuators, fluid inflow ports and a central suction passageway in the working end.
Figure 5B:
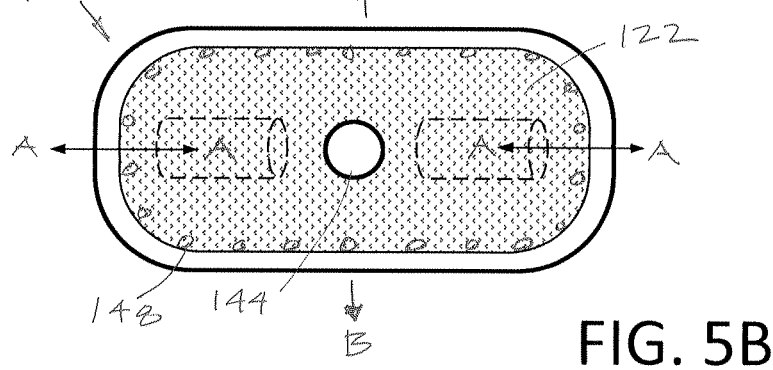
FIG. 5B is a front elevation view of another variation of a working end similar to that of FIG. 5A showing the location and orientation of linear actuators, fluid inflow ports and a central suction passageway.
Figure 5C:
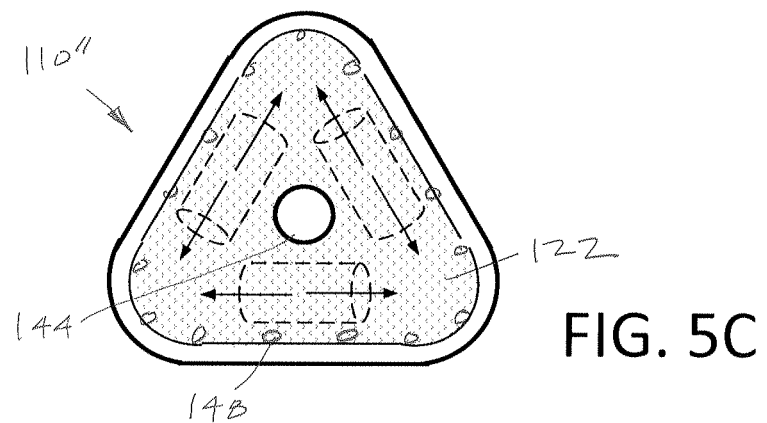
FIG. 5C is a front elevation view of another variation of a working end showing the location and orientation of linear actuators, fluid inflow ports and a central suction passageway.

FIGS. 5A-5B illustrate end view of other variations of skin contact surfaces 122 with outlines of LRAs and the direction of vibratory forces. FIG. 5A is a view of an applicator tip 110 as in FIGS. 2 and 3 and shows the direction vibratory forces AA. FIG. 5B shows a variation 110' in the shape of the skin contact surface 122 and again shows the direction of vibratory motion provided by the LRAs with arrows BB indicating the intended direction manual translation. FIG. 5C shows another variation 110" in which the LRA provides vibratory motion in multiple directions perpendicular to the axis of the device and there would not be a preferred direction of manual translation. Linear resident actuators of the type useful for the present invention can be obtained from Precision Microdrives Ltd. 105 Canterbury Court, 1 Brixton Road, London, SW9 6DE, United Kingdom.

Referring again to FIGS. 1-3, it can be understood further that the controller 155 can be configured to control the electrical source 150 that drives the LRAs, while contemporaneously controlling fluid flows from the fluid source 145 and the negative pressure source 140. In general, the variation shown in FIGS. 2 and 4 provides LRAs that can enhance skin abrasion with an abrasive applicator tip 110. The LRAs can provide sonic motion which may be in the range of 50 Hz to 1000 Hz for a skin abrasion mode of operation. The range of amplitude of the LRA can be from 0.005" to 0.25".

Figure 6A:
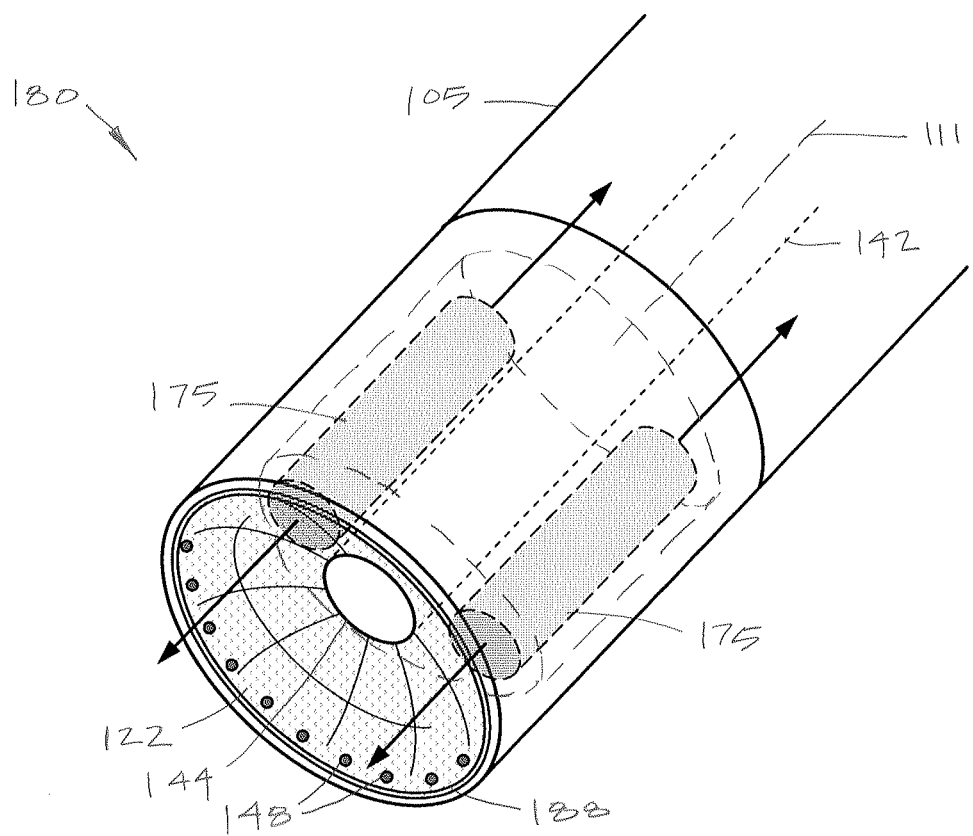
FIG. 6A is a perspective view of another variation of working end with the linear actuators configured to impart vibrational mechanical energy longitudinally relative to the longitudinal axis of the device shaft.
Figure 6B:
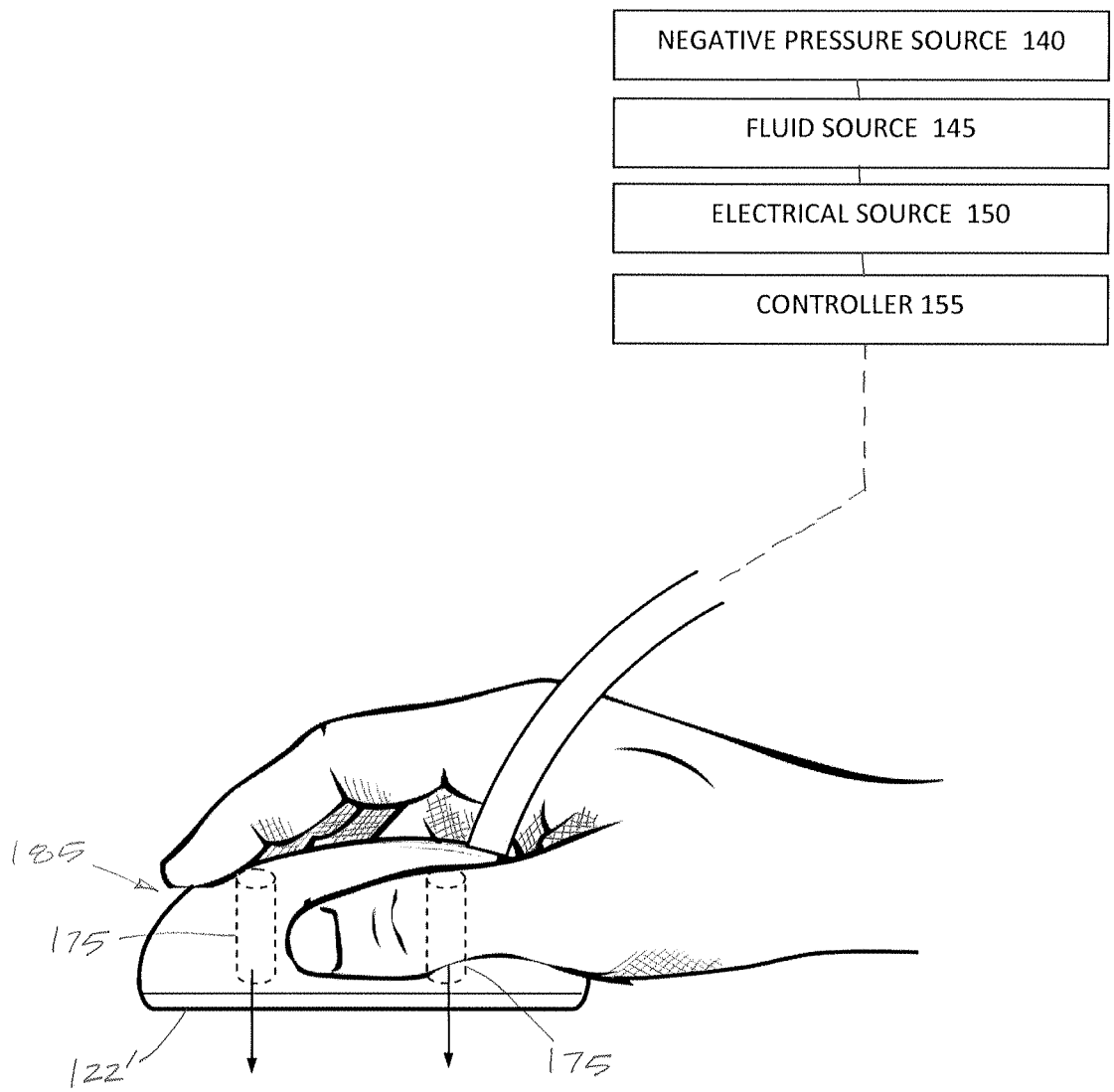
FIG. 6B is a perspective view of another embodiment of the skin treatment device and linear actuators in use being held by a human hand in relation to a patient's skin.

Now turning to FIGS. 6A and 6B, another applicator tip variation 180 is shown which uses LRAs 175 to provide a different mode of operation. In the variation shown in FIG. 6A, two LRAs are oriented substantially parallel to the axis 111 of the device body 105, or generally perpendicular to the skin contact surface 122. This applicator tip 180 may or may not have abrasive elements in the skin contact surface 122. In this variation, the LRAs 175 are adapted to operate in an "infusion mode" to infuse fluid from fluid source 145 into the patient's skin by means of vibratory forces being applied substantially perpendicular to a tensioned skin surface along with the fluid flows. FIG. 6B shows a handheld device 185 with a different form factor having a much larger skin contact surface 122' that again has at least one LRA 175 are oriented perpendicular to the skin contact surface 122'. The devices of FIGS. 6A-6B may be used following an abrasive skin treatment wherein these devices may be dedicated for use in enhancing fluid penetration into the patient's epidermis.

Figure 7A:
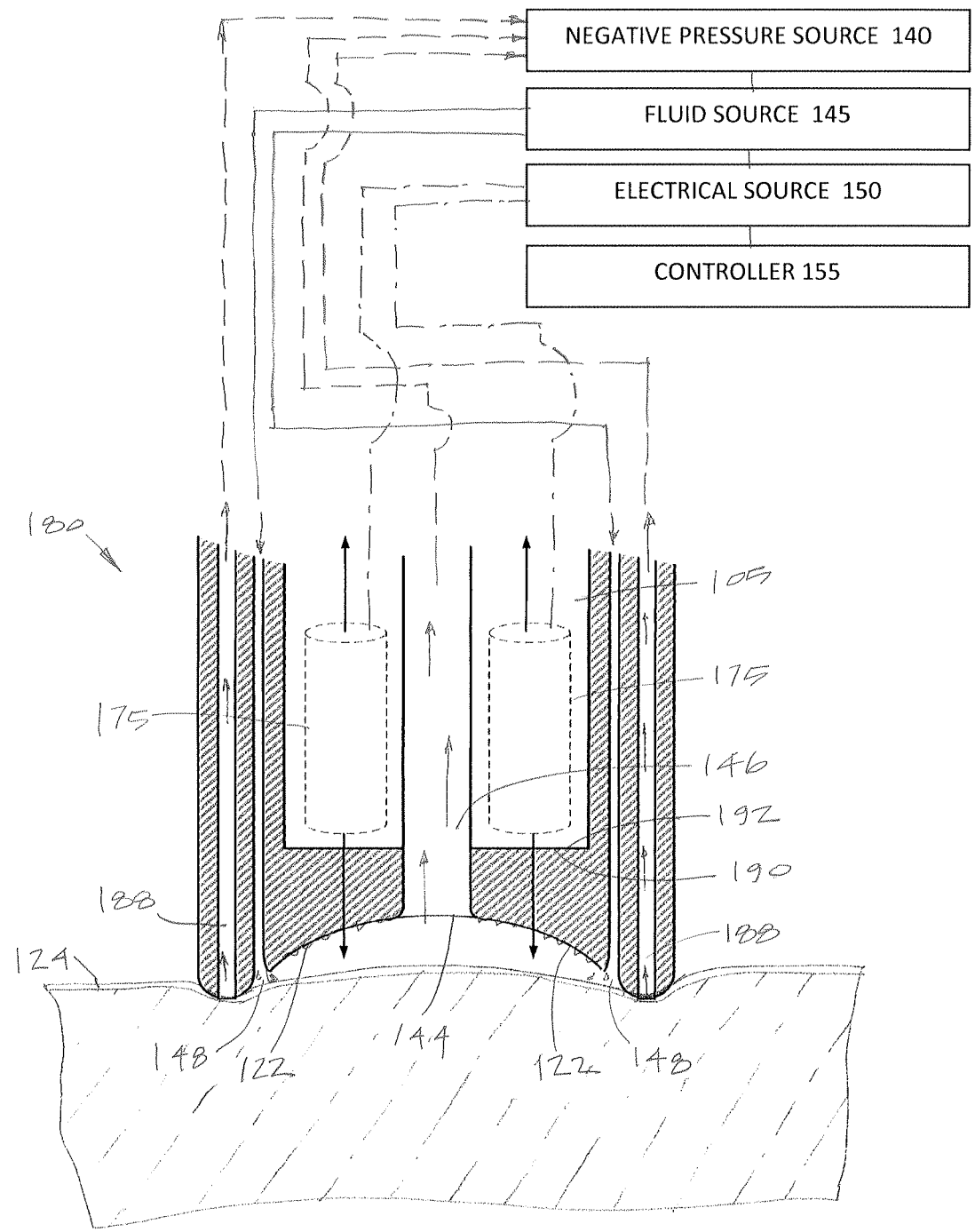
FIG. 7A is a sectional view of an initial step of using the working end of FIG. 6A to treat a patient's skin.
Figure 7B:
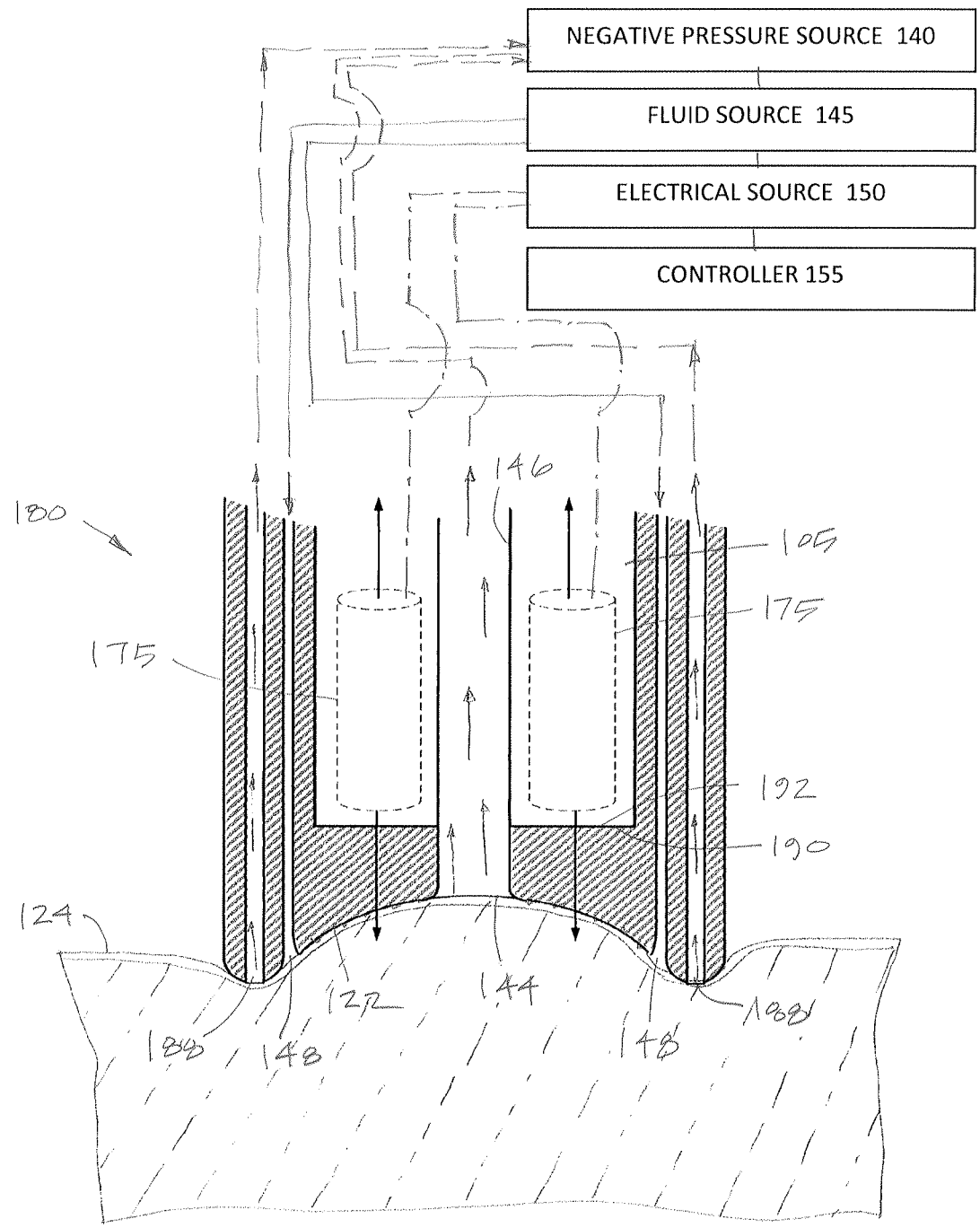
FIG. 7B is a sectional view similar to FIG. 7A showing subsequent step of actuating the negative pressure source, the fluid source and the linear actuators to treat the patient's skin.

As can be seen in FIGS. 6A and 7A, the applicator tip again has a central aspiration channel 142 communicating with central opening 144. In addition, the negative pressure source 140 communicates with a peripheral annular channel 188 (or set of ports). Thus, the patient's skin can be suctioned against the skin contact surface 122 at both the periphery and the center of the working end to capture and tension the skin surface. The central aspiration opening 144 and the peripheral aspiration channel 188 can be coupled to the same negative pressure source 140 or the controller 155 can control valves in the aspiration channels to modulate suction pressure in the ports 111 and 188. In one variation, referring to FIG. 7A, the controller 155 operates the system so that initially suction is applied through the perimeter aspiration channel 188 to engage the skins surface as shown in FIG. 7A. Thereafter, the controller 155 actuates the negative pressure source 140 to provide suction through the central opening 144 which results in stretching the skin into the concavity of the applicator tip 110 as shown in FIG. 7B. The controller 155 then further can operate an optional valve to allow fluid to flow from fluid source 145 through ports 148 to interface with the skin. The fluid flows can be provided by a positive pressure pump or can be influenced by the negative pressure at the skin surface through aspiration port 144. Finally, the controller 155 can actuate the LRAs contemporaneous with fluid flows to the skin interface, which provide mechanical force to infuse fluids into the stretched and abraded skin surface. The operator can actuate the system by a switch on the hand held device 100 or by means of a foot switch, or another suitable switching mechanism. Thus, in FIG. 7B can be seen by picturing motion of the LRA's assistant driving fluids perpendicularly into the epidermis. It is believed that they are between motion are useful for that influence the epidermis, for example from 500 Hz to 4000 Hz.

It can be understood from the FIGS. 2-7B that the LRAs 175 are carried in the device very close to the distal end of body 105 to allow the transmission of forces directly to and through the applicator tip 180 to the patient's skin. The device is designed so that a disposable applicator tip 180 can be attached to body 105 so that surface 190 of the tip 180 interfaces with surface 192 of body 105 to allow effective force transmission from the LRAs through the tip (see FIGS. 7A-7B).

Figure 8:
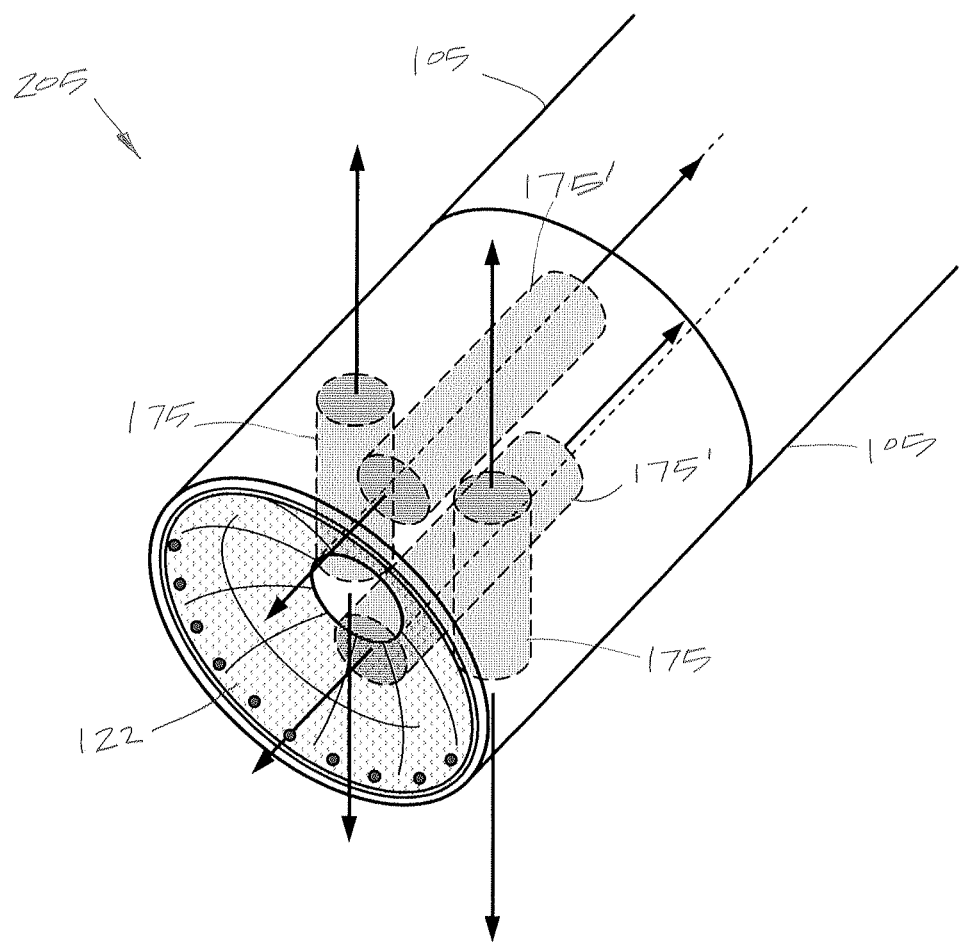
FIG. 8 is a sectional view of another variation of working end with multiple linear actuators configured to selectively impart vibrational energy to skin in a first axis and/or a second axis.

In another variation shown in FIG. 8, a device body 205 can be configured with multiple LRAs with at least one LRA 175 oriented to provide vibratory motion parallel to the skin surface for causing abrasion in an "abrasion mode" with at least one another LRA 175 oriented to provide vibratory motion substantially perpendicular to the skin surface to enhance fluid penetration into the patient's epidermis in an "infusion mode" as described above. In one system variation, the operator can select activation of the skin-parallel LRA motion or the skin-perpendicular LRA motion. In another system variation, the controller 155 can operate each LRA in pulsed intervals ranging from 0.1 seconds or more. Further, the controller 155 can be adapted to operate "abrasion mode" LRAs in a timed sequence with the "infusion mode" LRAs. The controller 155 can have presets or can be programmable to provide various overlapping or non-overlapping abrasion and infusion modes.

Figure 9:
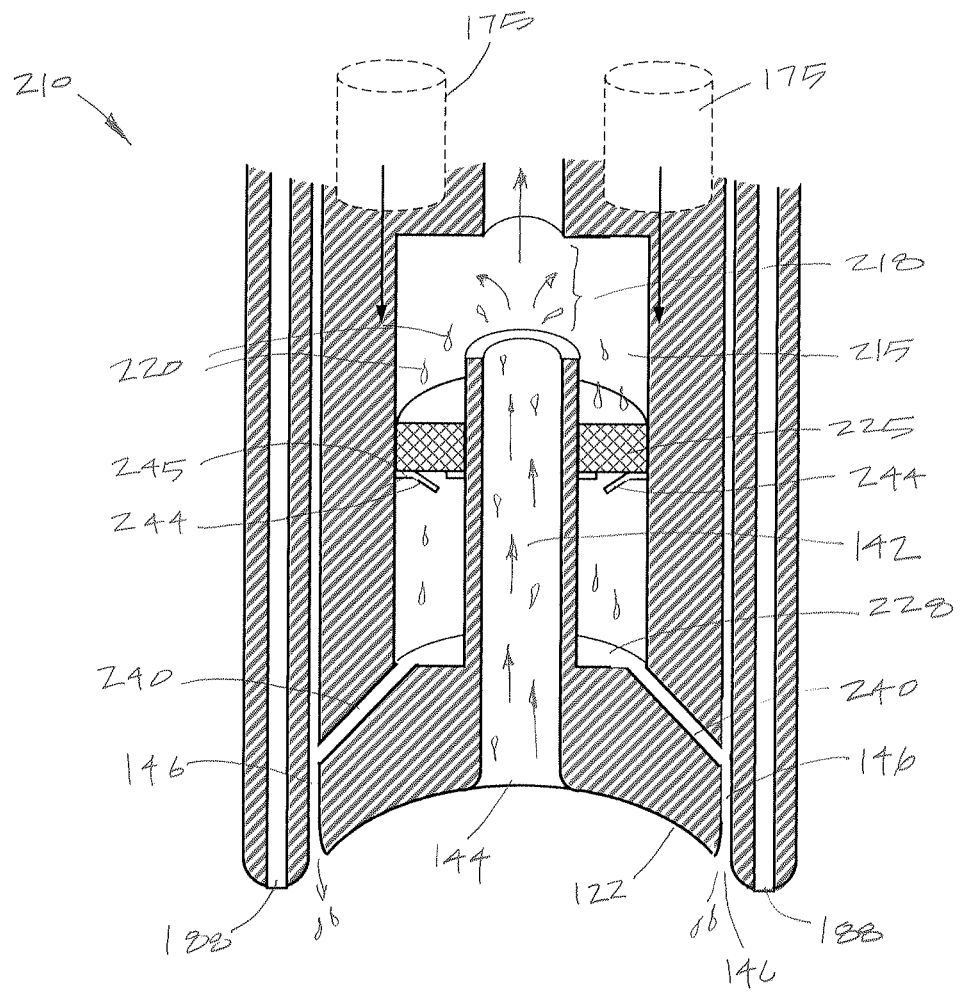
FIG. 9 is a sectional view of another variation of working end with a fluid trap and fluid recirculation mechanism.

FIG. 9 another embodiment another variation of an applicator tip 210 that includes a fluid trap for allowing the recirculation of therapeutic fluids. The applicator tip 210 of FIG. 9 is similar to the FIG. 7A, with central aspiration channel 142, peripheral aspiration channel 188 and a plurality of fluid inflow channels 148 in a concavity of the tip 210. The tip 210 can be disposable, and includes an interior collection chamber 215. As can be seen, the aspiration channel 142 extends partway through the collection chamber 215 and a gap 218 in the channel allows fluids in the outflows to separate from the aspirated gas flows. Thus, gravity will cause fluid droplets 220 to fall out of the aspiration pathway into chamber 215. The fluid droplets can pass through a filter indicated at 225 and then fall to the bottom 228 of chamber 215 and then through channels 240 back in the fluid inflow channels 148. By this means, therapeutic fluids that were not absorbed by the patient's skin may be re-introduced in to the interface with the skin for infusion therein. In one variation, shown in FIG. 9, the collection chamber 215 includes one-way valves 244, such as flaps in a silicone sheet 245 wherein aspiration pressure from negative pressure source 140 closes the valves 244 to prevent fluids or gas from being suctioned through recirculation channels 240. It can be understood that when the collected fluid reaches a certain weight in the chamber and when the operator intermittently stops operating the negative pressure source 140, then the captured fluids will fall through the one-way valves 244 into the bottom 228 of the collection chamber 215. In another variation, the controller 155 can intermittently turn off the negative pressure source 140 which will then allow the captured fluid volume to fall through the one-way valves 244 to the bottom 228 of the collection chamber 215. It can be seen in FIG. 9 that the LRAs 175 can be positioned proximate to the applicator tip 210 to provide vibratory motion as described previously. It should be appreciated that the applicator tip 210 of FIG. 9 can have any suitable dimensions to position the LRAs 175 into close proximity to the skin contact surface 122.

Figure 10:
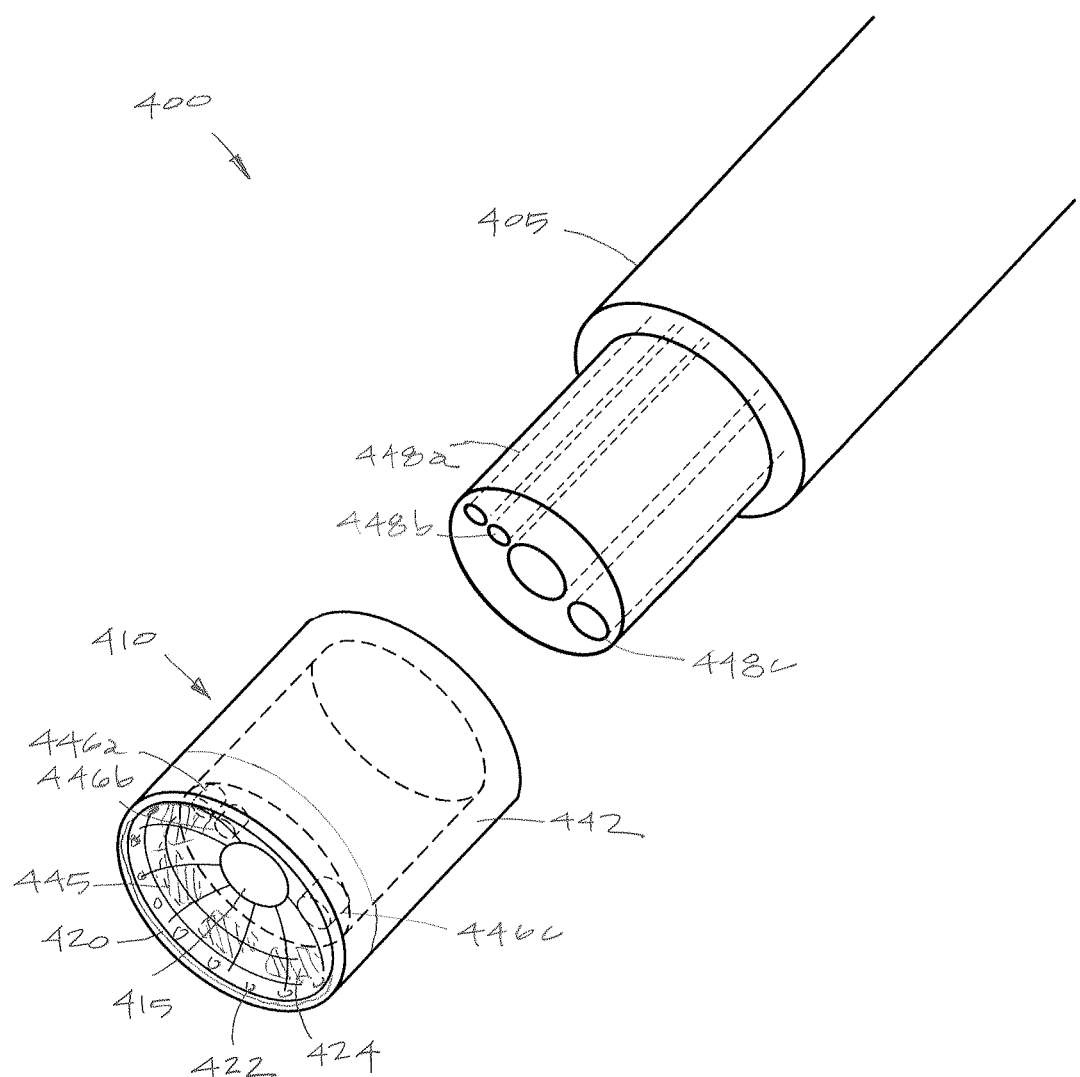
FIG. 10 is a perspective view of another variation of working end that includes a microfabricated microfluidic elastomer block with integrated channels for fluid flows and further configured with elastomeric actuators for treating a patient's skin.
Figure 11A:
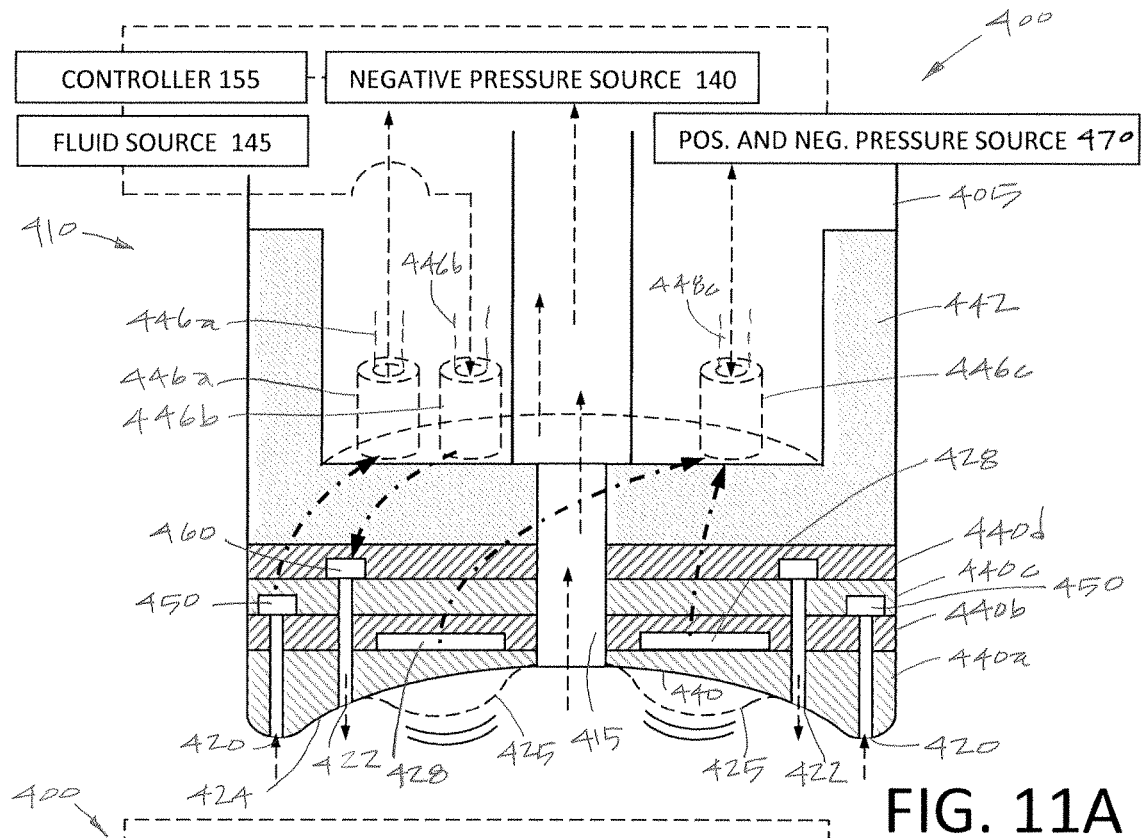
FIG. 11A is a sectional view of the working end of FIG. 10 in a first position showing fluid inflow channels and the suction channels with the elastomeric actuators in a repose or non-actuated position.
Figure 11B:
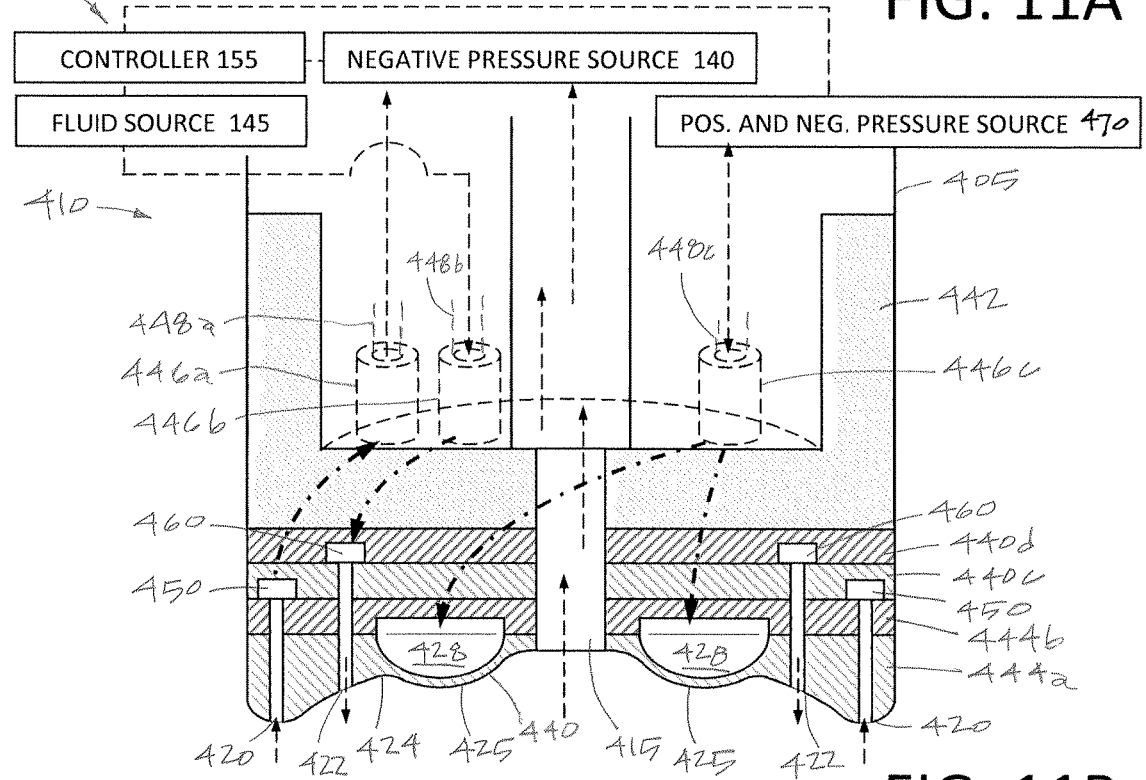
FIG. 11B is a sectional view as in FIG. 11A in a second position showing the elastomeric actuators in an actuated position.

FIGS. 10 and 11A-11B illustrate another variation of fluid-assisted microdermabrasion system 400 that utilizes a handheld device as described above with body 405 and an applicator tip 410 that utilizes a fluidic actuator instead of a linear resonant actuator or LRA 175 as describe above. In general, the applicator tip variations of FIGS. 10 and 11A-11B again are disposable tips with a central aspiration pathway passageway 415, a peripheral aspiration ports 420, and the plurality of fluid outflow ports 422 in the skin contact surface 424 as described previously. In addition, the applicator tip 410 includes one or more fluid actuators 425 which comprise pneumatic or hydraulic expandable interior chambers 428 that can actuate an elastomeric surface portion 440 of the applicator tip 410 as shown in FIGS. 11A-11B. There may be a single annular actuator or up to 20 or more actuators 425 in the skin contact surface 424. The actuators 425 of the type shown have "high amplitude" capabilities, when compared to amplitude of linear resonant actuators or sonic/ultrasonic skin treatment devices. Further, the frequency of actuation can be adjustable over a very wide range, for example from less than 1 Hz to 50 Hz or more.

Of particular interest, the applicator tip 410 comprises a microfabricated microfluidic body which can be manufactured by "soft lithography" means as is known in the art. There are several different techniques of microfabricating fluidic devices—all collectively known as soft lithography. For example, microtransfer molding is used wherein a transparent, elastomeric polydimethylsiloxane (PDMS) stamp has patterned relief on its surface to generate features in the polymer. The PDMS stamp is filled with a prepolymer or ceramic precursor and placed on a substrate. The material is cured and the stamp is removed. The technique generates features as small as 250 nm. Replica molding is a similar process wherein a PDMS stamp is cast against a conventionally patterned master. A polyurethane or other polymer is then molded against the secondary PDMS master. In this way, multiple copies can be made without damaging the original master. The technique can replicate features as small as 30 nm. Another process is known as micromolding in capillaries (MIMIC) wherein continuous channels are formed when a PDMS stamp is brought into conformal contact with a solid substrate. Then, capillary action fills the channels with a polymer precursor. The polymer is cured and the stamp is removed. MIMIC can generate features down to 1 µm in size. Solvent-assisted microcontact molding (SAMIM) is also known wherein as small amount of solvent is spread on a patterned PDMS stamp and the stamp is placed on a polymer, such as photoresist. The solvent swells the polymer and causes it to expand to fill the surface relief of the stamp. Features as small as 60 nm have been produced (see Xia and Whitesides, Annu. Rev. Mater. Sci. 1998 28:153-84).

Referring to FIG. 11A, it can be seen that the disposable soft lithography applicator tip 410 includes a base portion 442 of a rigid plastic for coupling with a device body 405, and plurality of microfabricated elastomer layers 444a-444d that include microfluidic channels, features, and components. In this variation, there are four elastomer layers 444a-444d, but it should be appreciated that there can be from 2 to 20 or more elastomer layers. As can be seen in FIGS. 10 and 11A, the applicator tip 410 has male flow connectors 446a-446c that couple with flow channels 448a-118c in the device body 442. For example, male connector 446a connects with flow channel 148a in body 405 that in turn communicates with the annular channel 450 and peripheral aspiration ports 420. FIG. 11A further shows flow channel 418a extends through the device body 405 and is operatively coupled to the negative pressure source 140. It can be understood that annular channel 450 in the fluidic tip 410 then communicates with a plurality of peripheral aspiration ports 420.

FIGS. 11A-11B further shows that male flow connector 446b couples with flow channel 448b in the device body and fluid source 145 to provide fluid flows to the skin contact surface 424 through outflow ports 422. Again, the male connector 446b connects with an annular channel 460 that extends around the applicator tip 410 to communicate with the ports 422.

Still referring to FIGS. 11-11B, the system 400 includes a reversible pump system or positive and negative pressure source 470 for actuating the actuators 425. In one variation, the pump system 470 can be an electro-mechanical pressure generator, such as an AC or a DC air pump. When operating to provide a vacuum or positive pressure, the source 470 can generate between 1 and 14 psi of force, for example. The pump system 470 can be a piston pump, or other pump type coupled to controller 155 that can deliver a precise limited volume of fluid pressure to the one more actuators 425. In FIGS. 11A-11B, the male flow connector 446c couples with flow channel 448c in body 442 and pressure source 470 to provide gas (or liquid) flows to chambers 428 of the actuators 425. The actuation of pressure source 470 and the actuators 425 is controlled by controller 155, which is synchronized with activation of the negative pressure source 140 and fluid source 145. In one variation, the operator depresses a trigger and the controller 155 activates the negative pressure source 140 to suction the patient's skin against the skin contact surface 424. The suction forces can draw fluid through ports 422 to the skin interface, or the controller 155 can release the fluid from source 145 a selected time interval later by controlling a valve. Thereafter, the operator can depress a trigger further (or actuate another trigger) to actuate the actuators 425. In one variation, the actuators 425 are controlled by controller 155 to operate at a predetermined frequency and amplitude. In another variation, the controller 155 can be configured to allow the operator to select from a multitude of actuator frequencies and amplitudes, for example on a touch screen of the controller 155.

In use, the system 400 of FIGS. 10-11B would allow the operator to strongly suction the patient's skin against the skin, contact surface 424 which will tension and stretch the engaged skin, and then the actuation of the actuators 425 will further tension and stretch the skin in the presence In another variation, the skin contact surface 424 can have abrasive elements (e.g., diamond particles, and the actuation of the actuators can cause motion in the abrasive over the patient's skin. This can be done in combination with a fluid infusion treatment.

Figure 12A:
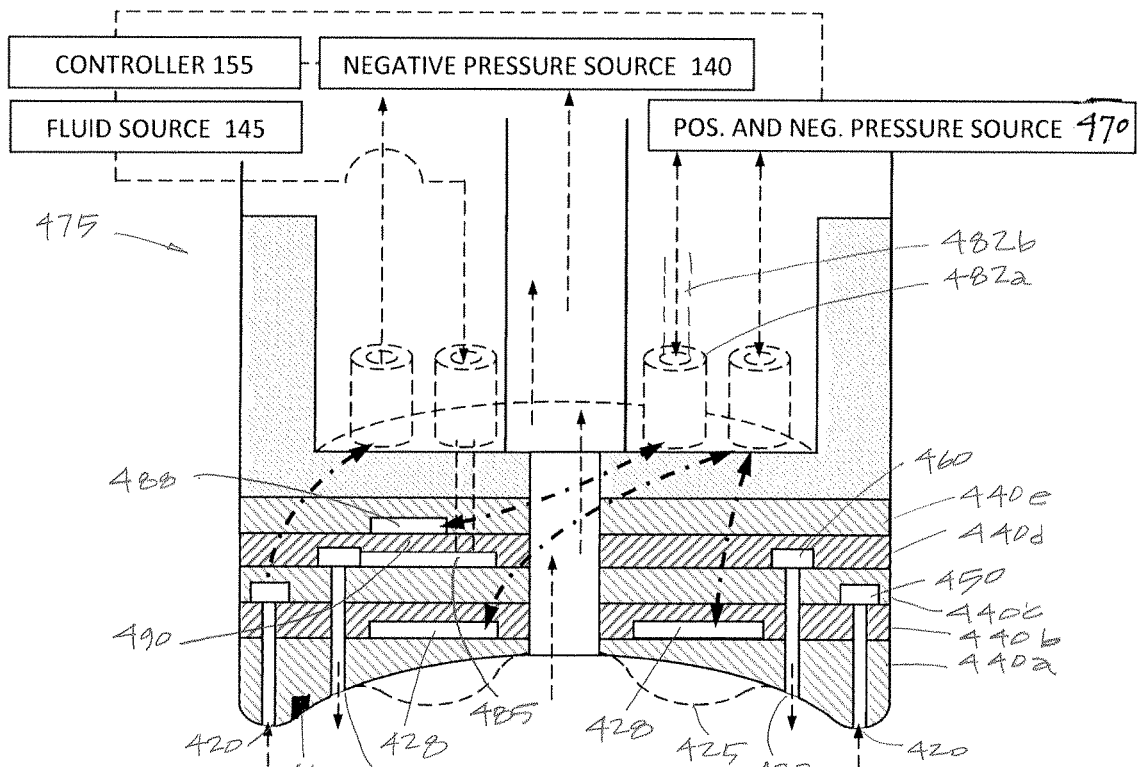
FIG. 12A is a sectional view of a working end similar to that of FIGS. 11A-11B with a microfabricated elastomeric valve operated by a controller to control fluid inflows, with the valve in a normally open position.
Figure 12B:
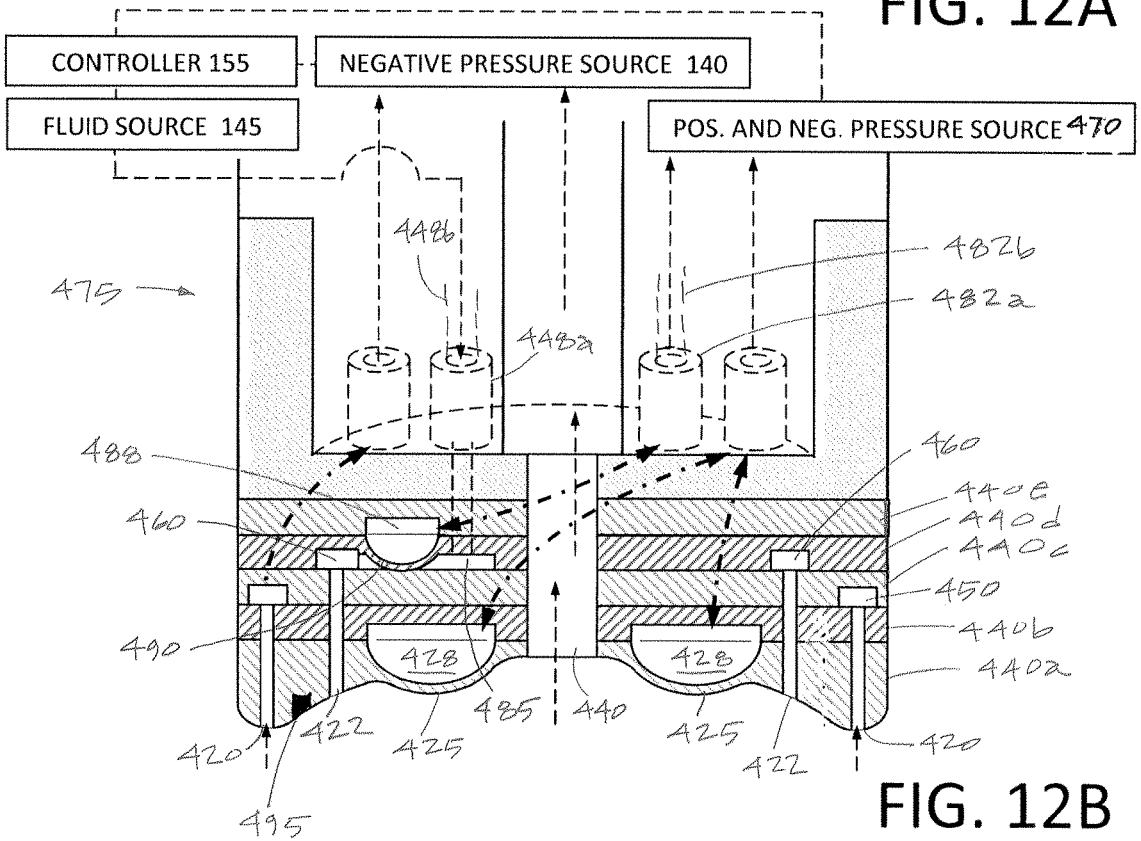
FIG. 12B is a sectional view of the working end of FIG. 11A with the valve in a closed position.

FIGS. 12A-12B illustrate another soft lithography applicator tip 475 that is similar to the embodiment of FIGS. 10-11B with actuators 425, fluid infusion channels 422 and aspiration channels 420 and 440. The tip 475 differs in that is includes an additional features comprising at least one fluidic valve 480 in elastomer layers 440a-440e of the tip. In FIG. 12A, it ea be seen that a male flow connector 482a couples with flow channel 482b in the device body and communicates with pressure source 470 operated by the controller 155 to and open and close an elastomeric valve 480. In this variation, the valve 480 opens and closes fluid flow channel 485 formed in the elastomer layers 440c-440d that communicates with fluid source 145. More in particular, the valve 480 operates by fluid (typically air) being pumped into chamber 488 by pressure source 470 which expands chamber 488 to cause elastomer wall 490 of layer 440d to impinge on and close flow channel 485 which communicates with annular channel 460 and the flow ports 422 in the skin contact surface 424. FIG. 12A shows valve 480 in an open position and FIG. 12A shows valve 480 in a closed position. In can be understood that controller 155 then operate the valve 480 to control delivery of therapeutics fluids from source 145 to the skin interface in cooperation with actuation of the actuators 425 and aspiration forces. The valve 480 can be used to conserve therapeutic fluids or to only introduce fluid when needed and can be operated manually or by the controller 155. A sensor, such as capacitance sensor 495 shown in FIGS. 12A-12B, can be coupled to controller 155 and can sense when whether the skin interface has adequate or inadequate fluid flows for a particular skin treatment. An applicator tip similar to that of FIGS. 12A-2B can be configured with a plurality of valves 480 or gates to direct flows from different fluid sources can be used, and such valves and gate can allow for computer control all operational parameters in all the channels. It should be appreciate that other forms of valves, normally open valves, normally closed valves, gates, one-way valves, check valves, pressure relief valves, flow control mechanisms and the like can be fabricated in an applicator tip 475 from elastomeric materials for obvious purposes of controlling and modulating flows in hydraulic and/or pneumatic circuits, and such elements can be of types used in fluidic chip fabrications and described in U.S. Pat. Nos. 6,951,632; 6,953,058; 6,802, 342; 8,590,573; 8,104,514; 7,640,947; 7,392,827 and 6,829, 753 which are incorporated herein by this reference.

Figure 13B:
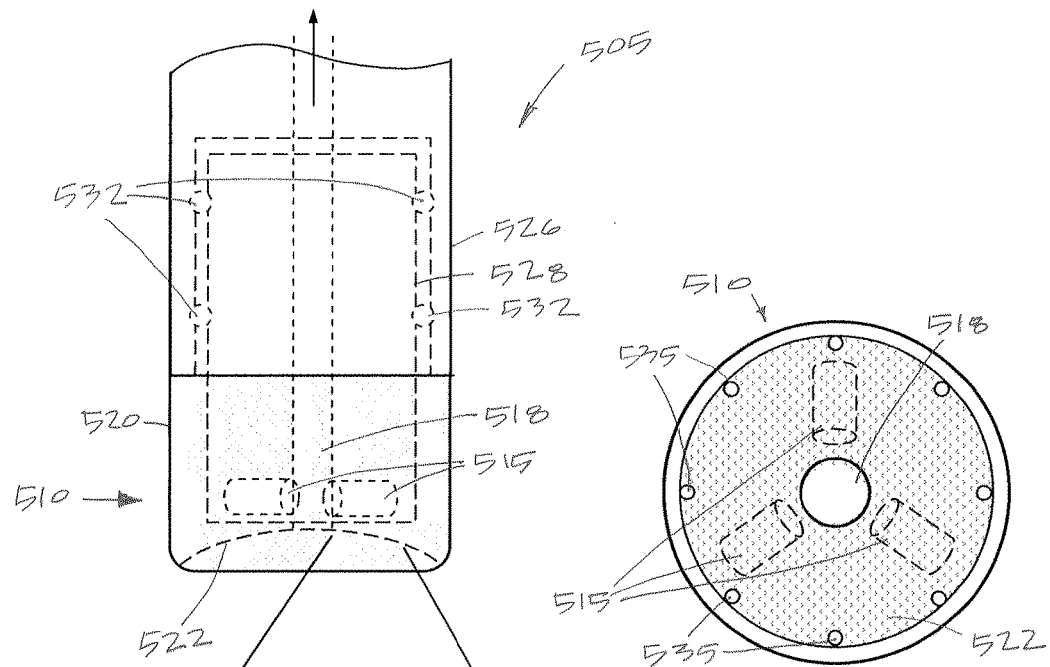
FIG. 13B is an end view of the working end of FIG. 13A.
Figure 13A:
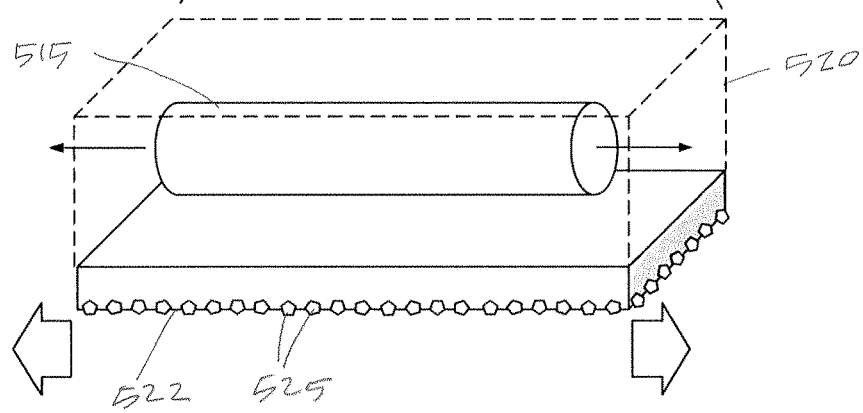
FIG. 13A is a schematic view of another variation of a working end with a floating component for maximizing the delivery of vibrational forces to a patients skin.

FIGS. 13A-13B illustrate another variation in which a hand held device 505 has a working end 510 that again carries at least one LRA 515 disposed around a central aspiration channel 518. The disposable applicator tip 520 is fabricated of an elastomer with a skin contact surface 522 having abrasive elements 525 disposed thereon. The LRAs 515 are adapted to stretch and impart motion to the skin to skin contact surface 522 parallel to the surface of the skin. In this variation, the device body 526 includes a floating body component 528 that carries the LRAs. It can be seen in FIG. 13A that soft resilient O-rings 532 carry the floating, vibrating body component within the device body 526. This allows for optimal transmission of vibration forces to the skin contact surface 522 and also prevents vibration of the device body 526.

In one variation shown in FIGS. 13A-13B, the working end carries three LRAs 515 with fluid inflow ports 535 and the fluid outflow channel 518 as described previously. In another variation, the floating body component 528 can carry first linear actuators to deliver forces for abrasion parallel to the skin and second linear actuators for to deliver forces perpendicular to the skin for fluid infusion. For example, a device can be similar to that of FIG. 8, with two LRAs for providing the abrasion mode, and a single LRA (e.g., a coin LRA) can be used to drive fluids into the patient's skin. In a variation, the fluid reservoir also can be carried in the handle and the user can simply squeeze a flexible fluid reservoir to provide for fluid infusion pressure. In one variation, the aspiration source can be coupled to the handle to make the entire system portable. In this variation, the only umbilical that is needed is a conduit to the negative pressure source which is configured to suction the patient's skin into the skin contact surface.

In another variation, an ultrasound wave generator such as a piezoelectric crystal can be provided in the working end to deliver waves at ultrasonic speeds to the skin, for example, in the range of 1 Mhz to 6 Mhz.

In another variation, the working end can include components and electrodes for delivering electrical current to the skin of a patient. In a further variation, the working end can be provided with a source of light energy, such as an LED or a flash lamp ot deliver light energy to the patient's skin, for example visible or infrared light.

Another variation can include a plurality of microneedles in the skin contact surface for creating microperforations in the skin, in order to deliver fluids or electrical currents into the patient's skin.

It should be appreciated that the treatment fluids can consist of water or an aqueous solution containing medications, peeling agents, serums, nourishing agents, botanicals, plumping agents, vitamins, hormones and the like known for topical use.

I claim:

1. A microdermabrasion system for treating a tissue for use with a fluid source and a negative-pressure source, the system comprising:

a device body having an applicator end, the applicator end comprising a tissue contact surface having a recess within the applicator end;

at least one fluid opening configured to deliver a fluid from the fluid source to the skin contact surface located towards an outer edge of the recess;

at least one negative pressure opening located at a center of the recess and fluidly coupled to the negative pressure source, such that application of the negative pressure source causes tissue to be drawn into the recess against the tissue contact surface, wherein when the tissue is positioned against the applicator end, the negative pressure source pulls the fluid from the at least one fluid opening; and at least one vibratory element positioned in the device body, where actuation of the vibratory element causes a vibratory motion of the applicator end such that the tissue contact surface applies a vibratory force to the tissue.

2. The microdermabrasion system of claim 1, where the tissue contact surface comprises an abrasive surface.

3. The microdermabrasion system of claim 1, where the tissue contact surface comprises a plurality of annular ridges and a plurality of recesses.

4. The microdermabrasion system of claim 1, where the at least one vibratory element comprises at least one vibratory element that produces vibration in a single direction relative to the device body.

5. The microdermabrasion system of claim 4, where the at least one vibratory element produces vibration in the single direction that is perpendicular to an axis of the applicator end.

6. The microdermabrasion system of claim 5, further comprising at least a second vibratory element that produces vibration in a direction perpendicular to the single direction of the at least one vibratory element.

7. The microdermabrasion system of claim 5, where the vibratory element is selected from either a linear resonant actuator or a fluid actuator.

8. The microdermabrasion system of claim 1, where the applicator end comprises a material configured to flex and/or compress slightly when engaging the tissue.

9. The microdermabrasion system of claim 1, where the tissue contact surface is concave.

10. The microdermabrasion system of claim 9, where the at least one fluid opening is located adjacent to an edge of the applicator end allowing the negative pressure source to pull the fluid from the at least one fluid opening adjacent to the edge.

11. The microdermabrasion system of claim 1, where the applicator end comprises an abrasive surface.

12. The microdermabrasion system of claim 1, where the applicator end comprises at least one aspiration channel.

13. The microdermabrasion system of claim 1, where the negative pressure source is in fluid communication with a vacuum lumen in the device body, and further comprising a fluid trap in fluid in the device body communication with the vacuum lumen.

14. A microdermabrasion system for treating a tissue and for use with a fluid source and a negative-pressure source, the system comprising:

a device body having an applicator end, the applicator end comprising a tissue contact surface forming a recess having an abrasive finish within the applicator end;

at least one fluid opening configured to deliver a fluid from the fluid source to the tissue contact surface located towards an outer edge of the recess;

at least one negative pressure opening located at a center of the recess and fluidly coupled to the negative pressure source, such that application of the negative pressure source causes tissue to be drawn into the recess against the abrasive finish, wherein when the tissue is positioned against the applicator end, the negative pressure source pulls the fluid from the at least one fluid opening; and at least one vibratory element positioned in the device body, where actuation of the vibratory element is configured to vibrate in a single axis, where the vibratory element causes a vibratory motion of the applicator end such that the tissue contact surface applies a vibratory force to the tissue.

15. The microdermabrasion system of claim 14, further comprising at least a second vibratory element that produces vibration in a direction perpendicular to the single axis.

16. The method of claim 14, where the recessed tissue contact surface comprises a plurality of annular ridges and a plurality of recesses.

17. The microdermabrasion system of claim 14, where the tissue contact surface is concave and where the at least one fluid opening is located adjacent to an edge of the applicator end such that the negative pressure source pulls the fluid from the at least one fluid opening adjacent to the edge.

* * * * *